United States Patent [19]

Gruening

[11] Patent Number: 4,977,186

[45] Date of Patent: Dec. 11, 1990

[54] WOOD PRESERVATIVE AND SOIL TREATMENT COMPOSITION

[75] Inventor: Rainer Gruening, Basking Ridge, N.J.

[73] Assignee: Troy Chemical Corporation, Newark, N.J.

[21] Appl. No.: 275,519

[22] Filed: Nov. 23, 1988

[51] Int. Cl.$^5$ ..................... A01N 37/34; A01N 47/10
[52] U.S. Cl. .................... 514/479; 514/478; 514/521
[58] Field of Search .............. 514/479, 478, 521

[56] References Cited

FOREIGN PATENT DOCUMENTS 56-26805 3/1981 Japan .................................. 514/479
2098069 11/1982 United Kingdom ................ 514/479

OTHER PUBLICATIONS

Bravery et al., "Artificial Weathering as an Aid to Assessing the Effectiveness of Chemicals for Preventing Blue Stain in Service—A Cooperative Service," International Research Group on Wood Preservation, (1984) Document No. IRG/WP/2215.
Barnes et al., "Treatment and Durability of Wooden Roofing Materials," Am. Wood-Preservers' Assoc. (1985).
Rutherford et al., "Loss of Pyrethroids from Treated Wood," Int. Biodeterioration Symp., (1983) 5:144–153.
Berry, "Recent Developments in the Remedial Treatment of Wood–Boring Insect Infestations," Int. Biodeterioration Symp. (1983) 5:154–165.
ICI Commercial Document entitled "Innovation," published by ICI Americas, Inc.

*Primary Examiner*—Allen J. Robinson
*Attorney, Agent, or Firm*—Banner, Birch, McKie & Beckett

[57] ABSTRACT

A composition for preserving wood or composite wood materials and for treating soil containing a compound selected from the group consisting of 3-iodo-2-propynyl-butyl carbamate, 3-iodo-2-propynyl hexyl carbamate, 3-iodo-2-propynyl cyclohexyl carbamate, 3-iodo-2-propynyl phenyl carbamate, and mixtures thereof, and at least one pyrethroid-type insecticide selected from the group consisting of cyano-(4-fluoro-3-phenoxyphenyl)-methyl-3-(2,2-dichloroethyl)-2,2-dimethylcyc lopropanecarboxylate, 3-phenoxyphenyl)-methyl-3-( 2,2-dichloroethenyl)-2,2-dimethyl-cyclopropanecarboxylate, cyano-(3-phenoxyphenyl)-methyl-3-(2,2-dichloroethenyl)-2,2-dimethyl-cycloprop anecarboxylate, cyano-(3-phenoxyphenyl)-methyl-2-(4-chlorophenyl)-3-methylbutyrate, and mixtures thereof.

13 Claims, No Drawings

1

WOOD PRESERVATIVE AND SOIL TREATMENT COMPOSITION

BACKGROUND OF THE INVENTION

1. Field of the Invention

The present invention relates to a composition useful for preserving wood and composite wood materials and for treating soil to protect against termite infestation. The present invention also relates to a process for treating wood and composite wood materials to preserve the wood, as well as to a process for treating soil to control termite infestation.

The invention specifically relates to a mixture of a fungicidally effective amount of a compound selected from the group consisting of 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof, and an insecticidally, e.g., termiticidally, effective amount of at least one pyrethroid-type insecticide selected from the group consisting of cyano-(4-fluoro-3-phenoxyphenyl)-methyl-3-(2,2-dichloroethenyl)-2,2-dimethyl-cyclopropanecarboxylate [Cyfluthrin], (3-phenoxyphenyl)-methyl-3-(2,2-dichloroethenyl)-2,2-dimethyl-cyclopropanecarboxylate [Permethrin], cyano-(3-phenoxyphenyl)-methyl-3-(2,2-dichloroethenyl)-2,2-dimethyl-cyclopropanecarboxylate [Cypermethrin], cyano-(3-phenoxyphenyl)-methyl-2-(4-chlorophenyl)-3-methyl-butyrate [Fenvalerate], and mixtures thereof, and to the use of this composition for wood preservation and soil treatment.

2. Description of Related Art

The compound 3-iodo-2-propynyl butyl carbamate (IPBC) (CAS 55406-53-6) is widely used as a fungicide for aqueous and organic solvent based systems such as paints and coatings, metal cutting fluids, textile and paper coatings, inks, plastics, adhesives and the like. Research indicates that IPBC also has a promising efficacy profile against wood destroying organisms (fungi), having shown low toxicity values for common fungi. Indeed, a unique characteristic of IPBC is its efficacy against both blue stain (ascomycetes) and general wood destroying fungi (basidiomycetes) at a reasonable application rate.

It also is known that pyrethroid-type insecticides including cyano-(4-fluoro-3-phenoxyphenyl)-methyl-3-(2,2-dichloroethenyl)-2,2-dimethyl-cyclopropanecarboxylate [Cyfluthrin], (3-phenoxyphenyl)-methyl-3-(2,2-dichloroethenyl)-2,2-dimethyl-cyclopropane-carboxylate [Permethrin], cyano-(3-phenoxyphenyl)-methyl-3-(2,2-dichloroethenyl)-2,2-dimethyl-cyclopropanecarboxylate [Cypermethrin], and cyano-(3-phenoxyphenyl)-methyl-2-(4-cholorphenyl)-3-methyl-butyrate [Fenvalerate] can be used as insecticides in soil treatment compositions used for protecting plants and wooden structures, in particular against termite infestation.

It generally is agreed that insecticides for plant protection should degrade after a certain period of time to eliminate the possibility of food chain contamination endangering the health of humans and wildlife. It also is recognized that to be effective, insecticides for plant protection generally should remain on the surface of the treated plant and not penetrate too deeply into the plant. In this way, the insecticides can be washed off the plant easily some time after the original application. These characteristics are the antithesis of properties needed for a successful wood or soil treatment composition, where long-term efficacy and good penetration of the active ingredients into the woody substrate or soil stratum are key attributes.

For complete protection, wood should be treated with a composition that not only prevents destruction from wood-destroying fungi, blue stain and molds but also from wood-destroying insects, for example such as termites. The prior art, however, does not provide any indication whether the combination of the fungicide IPBC or other related fungicides with one or more of the above-mentioned pyrethroid-type insecticides would be useful for wood protection. The prior art similarly fails to indicate whether such a combination would be useful for soil treatment.

While the pyrethroid-type insecticides of the above-mentioned group are known to exhibit good insecticidal activity, particularly against termites, it is not known whether these insecticides could also be used for wood preservation in combination with the fungicide IPBC or another related fungicide while retaining their termiticidal efficacy. Additionally, it is not known how the combination of the fungicide IPBC or another related fungicide with any of the above-mentioned pyrethroid-type insecticides would affect their termiticidal activity when used in a soil treatment composition. As is always a possibility when using a combination of chemicals having diverse activities, one of the chemicals may impair or interfere with the activity of the other.

Since the prior art has not disclosed or suggested combining IPBC or related compounds with the above-mentioned pyrethroid-type insecticides, the prior art does not indicate what amount of the fungicide IPBC and one or more of the above-noted pyrethroid-type insecticides is required to provide an optimum in wood preservation against both wood destroying and wood discoloring fungi and against wood destroying insects, especially termites. For similar reasons, it is not known what amount of IPBC and insecticide is needed to obtain the long-lasting efficacy needed for successful wood protection and soil treatment, or how to formulate an effective wood preservative or soil treatment composition using this biocide combination.

DISCLOSURE OF THE INVENTION

The present invention provides a composition useful for the long-term preservation of wood and composite wood materials against wood-discoloring and wood-destroying fungi, as well as against wood boring insects such as termites. The composition is particularly useful for protecting wood located adjacent to soil. In an alternate embodiment, the composition also is useful for treating the soil to control or prevent termite infestation.

For the purpose of this invention, a composite wood material is any product made from wood, such as plywood, pressed wood, chipboard, particle-board, wafer board, wood laminated material and the like.

In accordance with the present invention, a composition is provided which is useful for preserving wood and composite wood materials, and which also is useful for treating soil to protect against termite infestation. The composition contains a mixture of (a) a fungicidally effective amount of a compound selected from the group consisting of 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof, and (b) an insecticidally effective amount of at least one pyrethroid-type insecticide selected from the group consisting of cyano-(4-fluoro-3-phenoxyphenyl)-methyl-3-(2,2-dichloroethenyl)-2,2-dimethyl-cyclopropanecarboxylate, (3-phenoxyphenyl)-methyl-3-(2,2-dichloroethenyl)-2,2-dimethyl-cyclo-propanecarboxylate, cyano-(3-phenoxyphenyl)-methyl-3-(2,2-dichloroethenyl)-2,2-dimethylcyclopropanecarboxylate, cyano-(3-phenoxyphenyl)-methyl-2-(4-chlorophenyl)-3-methylbutyrate, and mixtures thereof.

The above-recited group of fungicides is represented by the formula:

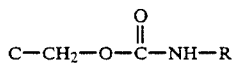

where R is butyl, hexyl, cylcohexyl or phenyl.

Generally, the composition also will include a liquid vehicle for dissolving or suspending the active fungicide and insecticide ingredients. The vehicle typically contains at least one of a diluent, an emulsifier and a wetting agent.

In still other aspects of the present invention, the composition also is provided with other adjuvants conventionally employed in wood preserving compositions such as organic binding agents, additional fungicides, auxiliary solvents, processing additives, fixatives, plasticizers, UV-stabilizers or stability enhancers, water soluble or water insoluble dyes, color pigments, siccatives, corrosion inhibitors, antisettlement agents, anti-skinning agents and the like. Additional fungicides used in the composition are preferably soluble in the liquid vehicle.

The wood preservative and soil treatment composition of the present invention generally comprises from about $2.0 \times 10^{-5}$ to 20 parts by weight, more generally from about 0.001 to 10 parts by weight, and most often from about 0.01 to 1.0 part by weight of a pyrethroid-type insecticide selected from the group consisting of cyano-(4-fluoro-3-phenoxyphenyl)-methyl-3-(2,2-dichloroethenyl)-2,2-dimethyl-cyclopropanecarboxylate, (3-phenoxyphenyl)-methyl-3-(2,2-dichloroethenyl)-2,2-dimethyl-cyclo-propanecarboxylate, cyano-(3-phenoxyphenyl)-methyl-3-(2,2-dichloroethenyl)-2,2-dimethyl-cyclopropanecarboxylate, cyano-(3-phenoxyphenyl)-methyl-2-(4-chlorophenyl)-3-methylbutyrate, and mixtures thereof per part by weight of a fungicide compound selected from the group consisting of 3-iodo-2-propynyl-butyl carbamate, 3-iodo-2-propynyl hexyl carbamate, 3-iodo-2-propynyl cyclohexyl carbamate, 3-iodo-2-propynyl phenyl carbamate, and mixtures thereof. With this relative proportion of the fungicide and insecticide ingredients one obtains a balance between the desired fungicidal and insecticidal activities in wood preserving and soil treatment applications. Preferably, about 0.01 to 5.0 parts by weight and more preferably about 0.05 to 1.0 part by weight of the pyrethroid-type insecticide is included in the composition per part by weight of the fungicide compound.

For practical uses, the composition typically is supplied as a preparation with the active ingredients dissolved or dispersed in a liquid vehicle or carrier material, such that the active fungicide and insecticide ingredients comprise from about 0.001% by weight up to about 10% by weight of the total composition, more generally from about 0.1% to 6% by weight, and most often from about 1 to about 5% by weight. In the case of a soil treatment preparation, the liquid vehicle normally comprises more than about 70% by weight, and more generally above about 90% by weight of the composition. For wood preservation applications, the liquid vehicle can constitute as little as 5% by weight of the preparation. The composition of the present invention can be provided as a ready-for-use product in the form of aqueous solutions and dispersions, oil solutions and dispersions, emulsions, aerosol preparations and the like or as a concentrate. The concentrate can be used as is, for example as an additive for plywood glues, or can be diluted prior to use with additional solvent or suspending agents.

The liquid vehicle is not a critical aspect of the present invention and any liquid which does not interfere with the fungicidal and insecticidal activities of the active ingredients and which is compatible with wood preserving or soil treatment applications potentially can be used in the present invention. Suitable diluents for the liquid vehicle include water and organic solvents including aromatic hydrocarbons, such as xylene, toluene, high aromatic petroleum distillates, e.g., solvent naptha, distilled tar oil and mixtures thereof; alcohols such as butanol, octanol and glycols; vegetable and mineral oils; ketones such as acetone; petroleum fractions such as mineral spirits and kerosene, and the like.

The diluent of the liquid vehicle generally comprises an organic solvent or solvent mixture. The liquid vehicle may contain at least one polar solvent, such as water, in admixture with an oily or oil-like low-volatility organic solvent, such as the mixture of aromatic and aliphatic solvents found in white spirits, also commonly called mineral spirits.

Oily or oil-like organic solvents useful in the present invention preferably have a flash point above about 28° C. and a boiling range (at atmospheric pressure) between about 130° C. to 250° C. while low-volatility organic solvents preferably have a flash point above about 55° C. and a boiling range (at atmospheric pressure) between about 180° C. to 350° C. The liquid vehicle is selected to enhance penetration of the active ingredients into the wood or soil being treated.

The liquid vehicle also will commonly include an emulsifier, a wetting agent, a dispersing agent or other surface active agent, particularly for soil treatment applications. Examples of suitable emulsifiers are those having an HLB value between about 10 and 14 commonly used for pesticide application. For example, Atlox 3406F and Atlox 3409F having an HLB value of 12 available from ICI can be used; as can nonylphenolethylene oxide ethers, and polyoxyethylene sorbitol esters or polyoxyethylene sorbitan esters of fatty acids. For example, a useful formulation for soil treatment applications may contain the mixture of the active fungicide and insecticide constituents dissolved in an organic solvent such as mineral spirits which in turn is emulsified with the aid of a suitable emulsifier in water as the primary liquid vehicle.

An aerosol preparation according to the invention is obtained in the usual manner by incorporating the active ingredients dissolved or suspended in a suitable solvent, in a volatile liquid suitable for use as a propellant, for example the mixture of chlorine and fluorine derivatives of methane and ethane commercially available under the trademark "Freon", or compressed air.

A soil treatment composition normally is applied by spraying. A sufficient amount of the composition is applied to the ground to be treated so that, based on the desired depth of treatment, one obtains an insecticidally (e.g., termiticidally) effective concentration of the active ingredients dispersed in the soil. To obtain an effective treatment, particularly against termites, it normally should be sufficient to apply between about 5 to 40 kilograms of the composition per square meter of ground area to be treated (about 1 to 8 pounds per sq. ft.), with an amount of about 10 to 20 kg/m$^2$ (about 2 to 4 lb/ft$^2$) being more typical.

In the case of a wood preservative, the balance of the composition may include additional ingredients known to be useful in wood preservatives and related products. Such ingredients include organic binding agents, such as alkyd resins, fixatives such as carboxymethylcellulose, polyvinyl alcohol, a paraffin and the like, co-solvents, such as ethylglycol acetate and methoxypropyl acetate and plasticizers such as benzoic acid esters and phthlates, e.g., dibutyl phthalate, dioctyl phthalate and diodecyl phthalate. Optionally dyes, color pigments, corrosion inhibitors, chemical stabilizers or siccatives (dryers) such as cobalt octate and cobalt naphthenate also may be included depending on specific applications.

The organic binding agent can be a chemically drying organic binder-forming polymer or a physically drying organic binder forming solids by solvent evaporation. Alkyd resins are one suitable class of organic binding agents. Other organic binding agents will be recognized by those skilled in the art. The organic binding agents may themselves be supplied in a liquid vehicle, and in that case the amounts referred to herein for the organic binder are on a solids basis.

Such additional ingredients are not essential to the practice of the present invention but are included in particular formulations to optimize overall effectiveness and ease of application. The specific examples of suitable constituents for a wood preservative preparation as enumerated above are not meant to be limiting and a wide variety of other possible ingredients will be recognized by those skilled in the art. Similarly, the quantity of such additional ingredients in any formulation is not critical. They generally can be used in an amount conventionally employed for products designed to be used in wood preserving applications. Normally, the totally formulated composition may contain from about 0.1% to 95% by weight, and more usually from about 1% to 50% by weight of these additional ingredients on a total solids basis.

The wood preservative composition can be applied by any of the techniques known in the art including brushing, spraying, dipping and the like. Generally, to obtain an effective treatment, it should be sufficient to apply between about 0.05 to 0.4 kilogram of the composition per square meter of wood surface area to be treated (about 0.01 to 0.08 pound per square foot), with an amount of about 0.1 to 0.2 kg/m$^2$ (about 0.02 to 0.04 lb/ft$^2$) being more typical.

The composition of the present invention can be prepared simply by mixing the various ingredients at a temperature at which they are not adversely affected, e.g., at a temperature of from about $-5°$ C. to 80° C., preferably at a temperature of from about 10° C. to 45° C. and at a pressure of 450 mm Hg to 900 mm Hg, preferably at about 650 mm Hg to 850 mm Hg. Preparation conditions are not critical. Equipment and methods conventionally employed in the manufacture of paint and similar compositions can be advantageously employed.

The following examples are illustrative of the present invention and not intended to be limiting.

EXAMPLE 1

A wood preservative useful for treating wood or composite wood materials with fungicidal and insecticidal activities, especially termiticidal efficacy, had the following composition (percent by weight):

| | |
|---|---|
| 3-iodo-2-propynyl butyl carbamate | 1.5% |
| cyano-(4-fluoro-3-phenoxyphenyl)-methyl-3-(1,2-dichloroethanyl)-2,2-dimethyl-cyclopropanecarboxylate | 0.2% |
| dibutyl phthalate | 5.0% |
| monitoring dye | 0.1% |
| mineral spirits (mixture of aliphatic and aromatic hydrocarbons, flash point above 50° C., boiling range 180° C. to 230° C.) | 93.2% |
| | 100.0% |

EXAMPLE 2

A wood preservative useful for impregnating wood or composite wood materials with primer effect having fungicidal insecticidal efficacy had the following composition (percent by weight):

| | |
|---|---|
| 3-iodo-2-propynyl butyl carbamate | 1.2% |
| (3-phenoxyphenyl)-methyl-3-(2,2-dichloroethenyl)-2,2-dimethyl-cyclopropanecarboxylate | 0.25% |
| alkyd resin (calculated on a solid basis) | 12.00% |
| dryer (cobalt octoate) | 0.1% |
| mineral spirits (mixture of aliphatic and aromatic hydrocarbons, flash point above 35° C. boiling range 145° C. to 200° C.) | 86.45% |
| | 100.0% |

EXAMPLE 3

A wood preservative concentrate useful for preparing a composition to be used for the impregnation of wood and composite wood materials had the following composition (percent by weight). The concentrate was diluted 1:4 with an organic chemical solvent mixture prior to the use.

| | |
|---|---|
| 3-iodo-2-propynyl butyl carbamate | 5.0% |
| cyano-(3-phenoxyphenyl)-methyl-3-(2,2-dichloroethenyl)-2,2-dimethyl-cyclopropanecarboxylate | 0.5% |
| ethyglycolacetate (co-sovlent) | 27.5% |
| dibutyl phthalate | 22.5% |
| mineral spirits (aliphatic and aromatic hydrocarbon mixture) boiling range 150° C. to 250° C. | 44.5% |
| | 100.0% |

EXAMPLE 4

A composition useful for the impregnation of wood and composite wood materials was prepared having the following composition:

| | |
|---|---|
| 3-iodo-2-propynyl butyl carbamate | 0.9% |
| cyano-(3-phenoxyphenyl)-methyl-butyrate | 0.25% |
| sorbitan fatty acid ester (emulsifier) | 5.5% |
| mineral spirits (mixture of aromatic hydrocarbons) | 24.0% |
| water | 69.35% |
| | 100.00% |

EXAMPLE 5

A composition useful for the impregnation of wood or composite wood materials with staining effect was prepared with the following ingredients (in percent by weight):

| | |
|---|---|
| 3-iodo-2-propynyl butyl carbamate | 1.3% |
| cyano-(4-fluoro-3-phenoxyphenyl)-methyl-3-(2,2-dichloroethenyl)-2,2-dimethyl-cyclopropanecarboxylate | 0.07% |
| alkyd resin (calculated as solid) | 21.5% |
| methoxypropylacetate (co-solvent) | 4.5% |
| siccative (cobalt napthenate) | 0.15% |
| methyl ethyl ketoxim (antiskinning additive) | 0.3% |
| bentonite clay (antisettlement additive) | 0.5% |
| dye and pigments | 2.5% |
| mineral spirits (mixture of aliphatic and aromatic hydrocarbons) | 69.18% |
| | 100.00% |

EXAMPLE 6

A composition useful for the impregnation of wood or composite wood materials exhibiting fungicidal and insecticidal effect was prepared with the following ingredients (in percent by weight):

| | |
|---|---|
| 3-iodo-2-propynyl butyl carbamate | 1.3% |
| cyano-)4-fluoro-3-phenoxyphenyl)-methyl-3-(2,2-dichloroethenyl)-2,2-dimethyl-cyclopropanecarboxylate | 0.08% |
| paraffin (fixative) | 4.0% |
| dibutyl phthalate | 5.0% |
| methoxypropylacetate | 7.0% |
| mineral spirits | 82.62% |
| | 100.00 |

The compositions of Example 1 through 6 can be used as a wood preservative simply by brushing or spraying the surface of the wood with these compositions or by dipping or soaking the wood product in the compositions. These compositions can be applied in an amount of about 0.05 to 0.4 kilograms per square meter to obtain satisfactory treatment.

EXAMPLE 7

A composition useful for treating soil to prevent or control termites can be prepared with the following ingredients (in percent by weight):

| | |
|---|---|
| 3-iodo-2-propynyl butyl carbamate | 3.0% |
| cyano-(3-phenoxyphenyl)-methyl-3-(2,2-dichloroethenyl)-2,2-dimethyl-cyclopropanecarboxylate | 1.0% |
| Organic solvent | 20.0% |
| Emulsifier | 5.0% |
| Water | 71.0% |

| | |
|---|---|
| | 100.00 |

The composition can be sprayed on the ground in an amount of about 5 to 40 kilograms per square meter in order to obtain effective termite control.

A surprising feature of the present invention is that the fungicide compounds enhance the effectiveness of the pyrethroid-type insecticides particularly against termites, even though when used alone, the fungicide compounds exhibit essentially no termiticidal activity.

While certain specific embodiments of the invention have been described with particularity herein, it will be recognized that various modifications thereof will occur to those skilled in the art and it is to be understood that such modifications and variations are to be included within the purview of this application and the spirit and scope of the appended claims.

I claim:

1. A composition useful for preserving wood or for treating soil for termite control comprising a termiticidally effective mixture of
   (a) a termiticidally enhancing effective amount of 3-iodo-2-propynyl butyl carbamate, and
   (b) an insecticidally effective amount of cyano-(3-phenoxyphenyl)-methyl-3-(2,2-dichloroethenyl)-2,2-dimethyl-cyclopropanecarboxylate.

2. The composition of claim 1 which includes a liquid vehicle containing at least one of a diluent, an emulsifier, or a wetting agent.

3. The composition of claim 1 containing from about $2.0 \times 10^{-5}$ to 20 parts by weight of said cyclopropanecarboxylate compound per part by weight of said carbamate compound.

4. The composition of claim 3 containing from about 0.001% to 10% by weight of said mixture of carbamate compound and cyclopropanecarboxylate compound.

5. The composition of claim 2 wherein said diluent is selected from the group consisting of an organic solvent and water.

6. The composition of claim 1 containing at least one of an organic binding agent, a fixative or a plasticizer.

7. The composition of claim 6 containing at least one of a dye, a pigment, or a stabilizer.

8. The composition of claim 2 wherein the liquid vehicle comprises a mixture of at least one organic solvent and water, said organic solvent having a low volatility with a flash point above about 28° C.

9. The composition of claim 8 wherein the said solvent includes an organic binding agent or fixative.

10. A method for preserving wood or composite wood material for termite control which comprises applying to the surface of said wood or composite wood material a termiticidally effective amount of the composition of claim 1.

11. The method of claim 10 wherein between about 0.05 to 0.4 kilograms of said composition are applied to a surface of said wood or composite wood material per square meter of said surface.

12. A method for treating soil for termite control which comprises applying to the surface of said soil a termiticidally effective amount of the composition of claim 1.

13. The method of claim 12 wherein between about 5 to 40 kilograms of said composition are applied per square meter of soil to be treated.

* * * * *